United States Patent
Wang et al.

(10) Patent No.: US 7,964,723 B2
(45) Date of Patent: Jun. 21, 2011

(54) AND PRACTICAL PROCESS FOR EXCLUSIVELY PRODUCING (S)-9-FLUORO-3-METHYL-10-(4-METHYL-1-PIPERAZINYL)-7-OXO-2,3-DIHYDRO-7H-PYRIDO-[1,2,3,DE][1,4]BENZOXAZINE-6-CARBOXYLIC ACID HEMIHYDRATE

(75) Inventors: Zheqing Wang, East Haven, CT (US); Lijan Shu, Dongyang (CN); Weifeng Guo, Dongyang (CN); HangChang Zhu, Dongyang (CN); Pingai Yang, Dongyang (CN); Xiaofeng Shen, Dongyang (CN); Chenming Jin, Dongyang (CN)

(73) Assignee: Apeloa-Kangyu (CN)

( * ) Notice: Subject to any disclaimer, the term of this patent is extended or adjusted under 35 U.S.C. 154(b) by 367 days.

(21) Appl. No.: 12/253,553

(22) Filed: Oct. 17, 2008

(65) Prior Publication Data

US 2010/0029937 A1     Feb. 4, 2010

Related U.S. Application Data

(60) Provisional application No. 61/137,661, filed on Aug. 2, 2008.

(51) Int. Cl.
*C07D 498/06* (2006.01)
*C07D 403/10* (2006.01)
(52) U.S. Cl. .................................... 544/101; 514/229.8
(58) Field of Classification Search ................... 544/101
See application file for complete search history.

(56) References Cited

U.S. PATENT DOCUMENTS 5,545,737 A    8/1996    Sato et al.

FOREIGN PATENT DOCUMENTS

| EP | 0206283 B1 | 1/1993 |
| JP | 62252790 A | 11/1987 |
| JP | 2006/111561 A | 4/2006 |
| JP | 2006111561 | 4/2006 |
| JP | 2006273718 | 10/2006 |
| WO | 03028664 A2 | 4/2003 |
| WO | 03045329 A2 | 5/2003 |
| WO | 03045329 A2 | 6/2003 |
| WO | 2004055025 A1 | 7/2004 |
| WO | 2006/009374 A1 | 1/2006 |
| WO | 2006030452 A1 | 3/2006 |
| WO | 2006/048889 A1 | 5/2006 |

OTHER PUBLICATIONS

Hayakawa, I., et al., "Synthesis and Antibacterial Activities of Optically Active Ofloxacin," Antimicrobial Agents and Chemotherapy, (1986) 29(1): 163-164.
Kitaoka, H, et al., "Effect of Dehydration on the Formation of Levoflaxacin Pseudopolymorphs," Chem. Pharm. Bull., (1995) 43(4): 649-653.
International Search Report for PCT/US2008/080740.

*Primary Examiner* — Kahsay T Habte
(74) *Attorney, Agent, or Firm* — Cantor Colburn LLP

(57) ABSTRACT

A novel and practical process for selectively producing a pyridobenzoxazine carboxylic acid hemihydrate (e.g., (S)-9-fluoro-3-methyl-10-(4-methyl-1-piperazinyl)-7-oxo-2,3-dihydro-7H-pyrido-[1,2,3-de] [1,4]benzoxazine-6-carboxylic acid hemihydrate) in high yield via crystallization from an organic solvent or a mixed organic solvent system containing a calculated amount of water released from sodium sulfate decahydrate under gradually heating.

21 Claims, No Drawings

AND PRACTICAL PROCESS FOR EXCLUSIVELY PRODUCING (S)-9-FLUORO-3-METHYL-10-(4-METHYL-1-PIPERAZINYL)-7-OXO-2,3-DIHYDRO-7H-PYRIDO-[1,2,3,DE][1,4]BENZOXAZINE-6-CARBOXYLIC ACID HEMIHYDRATE

CROSS REFERENCE TO RELATED APPLICATION

This application claims the benefit of U.S. Provisional Application No. 61/137,661 filed on Aug. 2, 2008, which is hereby incorporated by reference in its entirety.

BACKGROUND

Levofloxacin, a synthetic broad-spectrum antibacterial agent for oral and intravenous administration, chemically is a chiral fluorinated carboxyquinolone. The chemical name of the hemihydrate form is (−)-(S)-9-fluoro-3-methyl-10-(4-methyl-1-piperazinyl)-7-oxo-2, 3-dihydro-7H-pyrido-[1,2, 3-de] [1,4] benzoxazine-6-carboxylic acid hemihydrate (CAS Registry No. 138199-71-0).

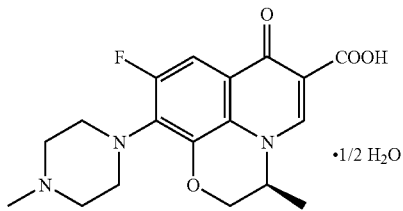

Levofloxacin is 8-128 times more potent in inhibiting the multiplication of gram-positive and gram-negative bacteria than its (+)-enatiomer, and approximately 2 times more active than its racemate, ofloxacine.

Three polymorphic forms (anhydrous α, β and γ) and two pseudopolymorphic forms (hemihydrate and monohydrate) of levofloxacin are reported by Kitaoka, H. et al in *Chem. Pharm. Bull.* 43 (4): 649 (1995). Levofloxacin hemihydrate is superior to the monohydrate as a drug substance in term of phase stability, one of the most important physical properties for pharmaceuticals.

The disclosed methods in JP-A-62-252790 or EP-0206283B for producing levofloxacin by means of crystallization of crude product from a solvent mixture of ethyl alcohol and ethyl ether or ammonia aqueous/ethanol solution may result in a mixture of levofloxacin hemihydrate and levofloxacin monohydrate.

To convert the formed monohydrate to hemihydrate is not practical. Although the contained water in the monohydrate can be vaporized via heating the crystals to result in the anhydrous form, which will absorb moisture, the anhydrous form only returns back to the original monohydrate, not the hemihydrate.

JP 2006111561 discloses a method of directly converting levofloxacin monohydrate to hemihydrate in tetrahydrofuran containing only 0.005% water. However, the yield is only 61%. The disadvantages are clear, an extra-manipulation step and loss of nearly 40% of the product.

To remove the monohydrate from contaminated levofloxacin hemihydrate via multiple recrystalizations is very labor and time intensive since both have very close solubility in solvents. Therefore, the recrystallization approach is impractical for manufacturing purposes.

The third solid state, the anhydrous crystal, is obtained by completely driving off crystal water from either the mono- or hemi-hydrate under elevated temperature. The anhydrate exhibits the problems of blockage and stickiness during industrial formulation processing. Thus, the dehydration of the hemi- and monohydrates is typically avoided by manufacturers.

U.S. Pat. No. 5,545,737 reports a method for selectively producing levofloxacin hemihydrate or monohydrate by controlling the water content of an aqueous solvent in which levofloxacin is dissolved during crystal formation. A single solvent such as ethanol, methanol, 1-propanol, 2-propanol or acetone is selected for the purpose.

WO 03/028664 discloses methods to produce crystal forms A, B, C, F, G, H as well as levofloxacin hemihydrate.

WO 03/045329 discloses slightly modified methods to purify levofloxacin hemihydrate via raising the dissolving temperature and adding an antioxidant such as metabisulfite or ascorbic acid into the crystallization solvent.

The methods given in WO 03/028664 and WO 03/045329 for preparing levofloxacin hemihydrate have disadvantages. The crude product is dissolved and heated in a solvent such as dimethylsulfoxide (DMSO, boiling point (bp) 189° C.), dimethyl acetamide (DMA, bp 164-166° C.), propylene-glycol-monomethyl ether (bp 118-119° C.), or n-BuOH (bp 117-118° C.) with/without water. Three potential risks may accompany these methods. The undesired monohydrate form may form during crystallization at high reflux temperatures. The hemihydrate may also be converted to the undesired anhydrous form during the course of removing the high boiling point solvents attached on the wet product under high temperatures and extended drying times. It is noted that U.S. Pat. No. 5,545,737 discloses the result of differential thermal analysis indicates that crystal water is liberated from the hemi- or mono-levofloxacin at about 70° C. under atmospheric pressure or at 60° C. under reduced pressure.

The possibility of contamination caused by residual antioxidant in the final product may occur and may interfere with the purity of the product.

Furthermore, acetonitrile used in the process of WO 03/028664 and WO 03/045329 belongs to Class II category listed in the Guidance for Industry, Q3C Impurities: Residual Solvents, U.S. Food and Drug Administration. As a Class II solvent, it is less desirable for use in the preparation of pharmaceutical products because of its inherent toxicity.

The yields of WO 03/028664 and WO 03/045329 for the crystallization are only in the range of 31-84%.

WO 2006/009374 A1 discloses a process for preparing levofloxacin hemihydrate or monohydrate of high purity. The purification experiments are operated in a mixed solvent system consisting of two organic solvents selected from ethyl acetate, methyl acetate, isobutyl methyl ketone, t-butyl alcohol and water. To overcome the difficulty of low solubility of the crude product in the solvent mixture, large volumes of organic solvents are needed, which greatly reduces the unit manufacturing capacity of reactors and increases the solvent consumption and labor costs.

WO 2006/048889 describes a process to prepare the hemihydrate in high purity. The complicated process includes pH-adjustments (4 times), de-colorizations (2 times), extraction with chlorinated solvent, such as dichloromethane (a Class II solvent), and crystallization in tetrahydrofuran (also a Class II solvent).

Of the described documents, the reported yields of crystal formation of levofloxacin hemihydrate are only around 70% to 85%. Low yield may partially be due to the loss of the product dissolved in large volumes of mother liquid.

Accordingly, there remains a need for a better process for manufacturing levofloxacin hemihydrate and related pyridobenzoxazine carboxylic acid hemihydrates.

SUMMARY

The present invention provides a novel process for exclusively generating pyridobenzoxazine carboxylic acid hemihydrate crystals, such as levofloxacin hemihydrate crystals, which are suitable for large scale manufacturing of these hemihydrates in term of high yield, low cost and easy manipulation.

In one embodiment, a process to selectively produce a pyridobenzoxazine carboxylic acid hemihydrate comprises mixing crude pyridobenzoxazine carboxylic acid and a calculated amount of sodium sulfate decahydrate in an anhydrous solvent system to form a mixture; heating the mixture to form pyridobenzoxazine carboxylic acid hemihydrate, wherein the pyridobenzoxazine carboxylic acid is of general formula (I):

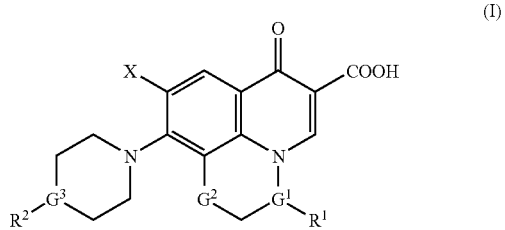

wherein X is halo; $G^1$ is carbon or nitrogen; $G^2$ is oxygen or carbon; $G^3$ is carbon or nitrogen; $R^1$ is $C_1$-$C_4$ alkyl; and $R^2$ is $C_1$-$C_4$ alkyl.

In another embodiment, a process to selectively produce a levofloxacin hemihydrate comprises mixing crude levofloxacin carboxylic acid and a calculated amount of sodium sulfate decahydrate in an anhydrous solvent system to form a mixture, wherein the anhydrous solvent system is a $C_1$-$C_4$ alkyl alcohol, a $C_3$-$C_4$ alkyl ketone, a $C_3$-$C_4$ alkyl ester, or combination thereof; heating the mixture to form levofloxacin hemihydrate; filtering the mixture to remove sodium sulfate to form a filtrate; optionally reducing the volume of the filtrate; cooling the filtrate to form levofloxacin hemihydrate crystals; and isolating the levofloxacin hemihydrate crystals substantially free of levofloxacin anhydrate or monohydrate.

DETAILED DESCRIPTION OF THE INVENTION

Disclosed herein is a convenient and industrially applicable process for selectively producing a crystalline pyridobenzoxazine carboxylic acid hemihydrate by heating a mixture containing a pyridobenzoxazine carboxylic acid and a calculated amount of sodium sulfate decahydrate in an anhydrous solvent system. The sodium sulfate decahydrate is the source of the hydrate water whereby the heating process releases the water of hydration from the sodium sulfate hydrate to the solvent system where the water is then available to form a hemihydrate with the pyridobenzoxazine carboxylic acid. The process has been found to selectively produce the pyridobenzoxazine carboxylic acid hemihydrate with no or substantially no formation of the monohydrate.

The pyridobenzoxazine carboxylic acid is of general formula (I):

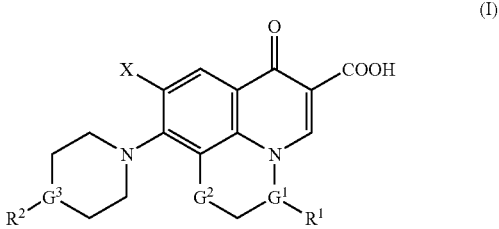

wherein X is halo, preferably fluoro or chloro, more preferably fluoro; $G^1$ is carbon or nitrogen, preferably, and more preferably carbon having an S stereochemical configuration; $G^2$ is oxygen or carbon, preferably oxygen; $G^3$ is carbon or nitrogen, preferably nitrogen; $R^1$ is $C_1$-$C_4$ alkyl, preferably methyl; and $R^2$ is $C_1$-$C_4$ alkyl, preferably methyl.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). The endpoints of all ranges directed to the same component or property are inclusive and independently combinable.

As used herein, "alkyl" is intended to include both branched and straight-chain saturated aliphatic hydrocarbon groups, having the specified number of carbon atoms. Thus, the term $C_1$-$C_4$ alkyl as used herein includes alkyl groups having from 1 to 4 carbon atoms. Examples of alkyl include, but are not limited to, methyl, ethyl, n-propyl, isopropyl, n-butyl, t-butyl, and isobutyl.

"Halo" or "halogen" as used herein refers to fluoro, chloro, bromo, or iodo.

In certain situations, the compounds of formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral high pressure liquid chromatography (HPLC) column.

In a specific embodiment, the pyridobenzoxazine carboxylic acid is (±)-9-fluoro-3-methyl-10-(4-methyl-1-piperazinyl)-7-oxo-2, 3-dihydro-7H-pyrido-[1,2,3-de][1,4]benzoxazine-6-carboxylic acid (ofloxacin).

In another specific embodiment, the pyridobenzoxazine carboxylic acid is (S)-9-fluoro-3-methyl-10-(4-methyl-1-piperazinyl)-7-oxo-2,3-dihydro-7H-pyrido-[1,2,3-de][1,4] benzoxazine-6-carboxylic acid (levofloxacin).

Sodium sulfate decahydrate ($Na_2SO_4 \cdot 10H_2O$) is a nontoxic, odorless crystal or granule. It is fairly chemically inert and has minimal health and safety concerns when inhaled or comes into skin contact. Sodium sulfate decahydrate releases its water gradually with heating. At its melting point of 32.4° C., the crystals of decahydrate release its water of hydration. Sodium sulfate decahydrate dissolves in 1.5 parts of water at 25° C. and in 3.3 parts of water at 15° C. and its aqueous solution is neutral (pH 6.0-7.5). It is insoluble in methanol and ethanol.

Sodium sulfate decahydrate is used as the source of crystal water in the present process due to its combined advantages of physical properties, chemical stability, and physical safety.

The formation of the hemihydrate is performed in an anhydrous solvent system. As used herein "solvent system" means a single solvent or a mixture of solvents. Preferably, the solvent system used in the instant process is miscible with water and has a limited solubility for the pyridobenzoxazine carboxylic acid hemihydrate. Suitable solvents for the solvent system include $C_1$-$C_4$ alkyl alcohols, $C_3$-$C_4$ alkyl ethers, $C_3$-$C_4$ alkyl ketones, $C_3$-$C_4$ alkyl esters, acetonitrile, dimethylformamide, or a combination thereof; preferably $C_2$-$C_3$ alkyl alcohols, acetone, methyl acetate, or a combination thereof.

In one embodiment, the solvent of the solvent system is a Class III solvent listed in the Guidance for Industry, Q3C Impurities: Residual Solvents, U.S. Food and Drug Administration. Class III solvents are regarded as less toxic and of lower risk to human health than Class II solvents. Exemplary Class III solvents include acetone, 1-butanol, 2-butanol, butyl acetate, tert-butylmethyl ether, ethanol, 2-ethoxyethanol, ethyl acetate, ethyl ether, isobutyl acetate, isopropyl acetate, methyl acetate, 3-methyl-1-butanol, methylethyl ketone, methylisobutyl ketone, 2-methyl-1-propanol, 1-pentanol, 1-propanol, 2-propanol, propyl acetate, or a combination thereof.

Although less desirous, certain Class II solvents can be used in the solvent system, including for example, acetonitrile, 1,2-dimethoxyethane, dimethylacetamide, dimethylformamide, 1,4-dioxane, ethyleneglycol, methanol, 2-methoxyethanol, and combinations thereof.

In one embodiment, the solvent system has a low boiling point, allowing for the solvent system to be removed smoothly during a drying course. Exemplary low boiling points are those lower than 85° C., preferably lower than 70° C., and more preferably lower than 60° C. as determined at atmospheric pressure.

In one embodiment, the solvent system is ethanol, 1-propanol, 2-propanol, methyl acetate, acetone, or a combination thereof; preferably a combination of ethanol and methyl acetate or a combination of ethanol and 2-propanol.

U.S. Pat. No. 5,545,737 discloses the use of crystallization solvents having a water content in the range of 4-5% (w/w) for use in preparing levofloxacin hemihydrate. It has been surprisingly found that to selectively form levofloxacin hemihydrate crystals the solvent system can have a water content as low as 2.0% (w/w), which is generated from the sodium sulfate decahydrate under gradual heating of the environment.

Accordingly, the ratio of the weight of sodium sulfate decahydrate to the weight of crude pyridobenzoxazine carboxylic acid can be as low as 0.2:1.0. The amount of sodium sulfate decahydrate can be in a ratio of 0.2 to 0.8 sodium sulfate decahydrate: 1.0 crude pyridobenzoxazine carboxylic acid (w/w); preferably 0.3 to 0.7 sodium sulfate decahydrate: 1.0 crude pyridobenzoxazine carboxylic acid (w/w); more preferably 0.4 to 0.6 sodium sulfate decahydrate: 1.0 crude pyridobenzoxazine carboxylic acid (w/w); and still yet more preferably 0.45 to 0.55 sodium sulfate decahydrate: 1.0 crude pyridobenzoxazine carboxylic acid (w/w).

To prohibit the hemihydrate from being contaminated by formation of the monohydrate, the ratio of sodium sulfate decahydrate to the weight of crude pyridobenzoxazine carboxylic acid should be no higher than 0.8:1.0 (w/w).

In one embodiment, the ratio of the weight of sodium sulfate decahydrate to the weight of crude levofloxacin is 0.3 to 0.6:1.0.

The ratio of the weight of the crude pyridobenzoxazine carboxylic acid to the volume of the solvent system is 1:5 to 16 (w/v), preferably 1.0:6 to 12 (w/v), more preferably 1.0:7 to 11 (w/v), still more preferably 1.0:8 to 10 (w/v), and yet more preferably 1.0:8.5 to 9.5 (w/v), which is suitable for economical manufacturing.

The crystallization heating temperature can be in range of 20° C. to 75° C., which consists of two stages. During the first stage there is a slow heating from 20° C. to 33° C., preferably 25° C. to 30° C., to allow the water to be released from sodium sulfate decahydrate. The time for the first stage of heating is 1 to 2 hours. During the second stage, the heating is maintained at 33° C. to 75° C., preferably from 40 to 65 ° C., and yet more preferably from 48 to 57° C. The time for allowing the hemihydrate to form can be from 2 to 10 hours, preferably 3 to 7 hours, and more preferably from 4 to 5 hours.

After heating period has ended the mixture is subject to filtration to remove sodium sulfate and, if used, activated carbon. The filtrate can be reduced in volume to promote hemihydrate crystal formation. After reducing the appropriate volume of solvent by techniques well known in the art (e.g., evaporation), pure hemihydrate seed crystals may be optionally added to help in the formation of the desired crystals.

The filtrate is then cooled down to 0 to 20° C., preferably 5 to 15° C., and more preferably 8 to 10° C., to promote crystallization. The cooling time can be in range of 2 to 15 hours, preferably 3 to 12 hours, more preferably 4 to 10 hours, and yet more preferably 5 to 8 hours.

The process may include the use of activated carbon to provide for decoloration and purification of the crude pyridobenzoxazine carboxylic acid.

In one embodiment, the activated carbon and sodium sulfate decahydrate are added to a mixture of crude pyridobenzoxazine carboxylic acid and solvent system. The resulting mixture can be stirred with heating for a certain period of time prior to filtration to remove the sodium sulfate and activated carbon. The collected sodium sulfate and activated carbon can be treated as waste.

In an alternative embodiment, the crude pyridobenzoxazine carboxylic acid can be decolorized with activated carbon in solution, warm-filtered, and subsequently cooled to ambient temperature prior to the addition of the sodium sulfate decahydrate. The mixture can then be re-heated and maintained at a targeted temperature for a certain period. The sodium sulfate can then be collected by filtration and the recovered sodium sulfate can be used as a reusable chemical reagent after a simple treatment.

The activated carbon may be used in an amount of 1 to 5% of the weight of crude pyridobenzoxazine carboxylic acid, preferably 2 to 4%, and more preferably 2.5 to 3.5% of the weight of crude pyridobenzoxazine carboxylic acid.

It was surprisingly found that the yields of the obtained hemihydrate crystals prepared by the methods described in this invention are all nearly quantitative. Not wishing to be bound by any particular theory, the quantitative yield may be attributed to the crystal solution being saturated by the sodium sulfate during and after the hemihydrate is formed, thereby the significantly reducing the solubility of levofloxacin hemihydrate crystals in the solvent. Accordingly, the products remaining in the mother liquid are substantially reduced.

*Chem. Pharm. Bull.* 43 (4): 649 (1995) and U.S. Pat. No. 5,545,737 describe drying the wet levofloxacin hemihydrate crystals at around 70° C. under atmospheric pressure or at around 60° C. under reduced pressure will force crystal water to be lost resulting in the formation of the anhydrous form.

Specified drying conditions are described herein to ensure the pyridobenzoxazine carboxylic acid hemihydrate product does not lose water and convert to the anhydrous state during the drying process.

Levofloxacin hemihydrate contains a theoretical amount of water of 2.43%. It has been found that 0.20-0.30% of water is lost by drying at 50° C. under vacuum of around 60 mm/Hg for a couple of hours, suggesting part of the hemihydrate product has been converted to the anhydrous form.

To prevent conversion to the anhydrous form, the pyridobenzoxazine carboxylic acid hemihydrate, such as levofloxacin hemihydrate, is dried at a temperature of 20 to 50° C., preferably 25 to 45° C. accompanied by a vacuum of 20 to 100 mm/Hg, preferably 40 to 180 mm/Hg depending upon the solvent system used in the process. In one embodiment, the drying conditions are 30 to 40° C. under a vacuum of 60 to 80 mm/Hg.

In embodiment, when a solvent having a boiling point of greater than 85° C. (e.g., 1-propanol or 2-propanol) is used as the solvent system, the collected hemihydrate product is rinsed with a lower boiling point solvent system (e.g., ethanol or acetone) one or more times before drying.

In one embodiment, an inert atmosphere (e.g., nitrogen, argon, and the like) flow is introduced during the drying operation until a constant weight is reached. Use of an inert atmosphere flow has been found to effectively shorten the drying time and allows for the use of a lower drying temperature.

The levofloxacin hemihydrate obtained by the processes herein exhibits powder X-ray diffraction and IR patterns that are both identical to that reported by U.S. Pat. No. 5,545,737 and *Chem. Pharm. Bull.* 43 (4): 649 (1995). C.H.N. elemental analysis and Karl-Fischer's water content analysis are both consistent with the calculated hemihydrate. Differential scanning calorimetry (DSC) spectra and melting point were found to be the same as for standard samples of the hemihydrate.

The analytical result to determine the presence of residual inorganic materials shows no sodium sulfate remains in the final product.

In one embodiment, the process produces levofloxacin hemihydrate substantially free of the anhydrate or monohydrate forms. As used herein, "substantially free" means less than 2 weight percent of the undesired form, preferably less than 1 weight percent, and more preferably less than 0.5 weight percent of the undesired form based on the total weight of levofloxacin.

The following examples are intended to illustrate and describe the benefits of the present invention, rather than to exemplify the full scope of the invention.

EXAMPLE 1

The Preparation of Levofloxacin Hemihydrate in Ethanol

Crude levofloxacin (100 g, containing 1.3% of water) is placed into anhydrous ethanol (900 ml) followed by activated carbon (3.0 g). The mixture is heated to 70° C.-75° C. for 30 minutes. The decolorized mixture is filtered. The clean filtrate is cooled to 15° C.-20° C. followed by the addition of sodium sulfate decahydrate (44.0 g). The mixture is slowly heated to 33° C.-35° C. during one hour and continuously heated at 65° C.-70° C. for 2 hours. The hot suspension is filtered.

The sodium sulfate is collected and rinsed with hot ethanol (60 ml×2). The combined filtrates are carefully concentrated and the mixture is reduced in volume to 300-350 ml. The resulting slurry is cooled by cooled water around 10° C.-15° C. for 3 hours. The precipitated crystals are collected by filtration, rinsed with cooled ethanol (100 ml). The wet product is dried under vacuum around 80-90 mmHg and at a temperature of 30° C.-35° C. under nitrogen flow to give product of 98.8 g (yield of 96.5%) with the purity of 99.8% (HPLC).

Melting point: 223° C.-225° C. (decomposed.)

Elemental analysis: Calculated: C, 58.37; H, 5.71; N, 11.35; Found: C, 58.34; H, 5.62; N, 11.38.

Water content (Karl-Fischer's Method): Calculated 2.43%, Found 2.42%.

IR: characteristic peak: 3440 cm-1

Powder X-Ray Diffraction Analysis: The pattern is the same with levofloxacin hemihydrate standard.

EXAMPLE 2

The Preparation of Levofloxacin Hemihydrate in Ethanol

Crude levofloxacin (100 g) is placed into anhydrous ethanol (800 ml) followed by adding sodium sulfate decahydrate (30.0 g) and activated carbon (3.0 g). The mixture is slowly heated to 33° C.-35° C. during one hour and continuously heated at 65° C.-70° C. for 2 hours. The hot suspension is filtered.

The sodium sulfate and charcoal are colleted and rinsed with hot ethanol (60 ml×2). The combined filtrates are slightly cooled, carefully seeded with pure crystals of levofloxacin hemihydrate and then concentrated to a volume of around 300 ml. The slurry is cooled around 10° C.-15° C. for 3 hours. The precipitated crystals are collected by filtration and rinsed with cooled ethanol (100 ml). The wet product is dried under vacuum around 80 mmHg and at the temperature of 35° C.-40° C. under nitrogen flow to give a product of 99.6 g (yield of 97.2%) with the purity of 99.7% (HPLC).

Melting point: 223° C.-225° C. (decomposed.)

Elemental analysis: Calculated: C, 58.37; H, 5.71; N, 11.35; Found: C, 58.35; H, 5.68; N, 11.40.

Water content (Karl-Fischer's Method): Calculated 2.43%, Found 2.46%.

IR: characteristic peak: 3440 cm-1

Powder X-Ray Diffraction Analysis: The pattern is the same with levofloxacin hemihydrate standard.

EXAMPLE 3

The Preparation of Levofloxacin Hemihydrate in Mixed Solvent System of Ethanol and 2-propanol Crude levofloxacin (140 g) is placed into a mixed system of ethanol (800 ml) and 2-propanol (800 ml) followed by the addition of sodium sulfate decahydrate (60 g) and activated carbon (4.0 g). The mixture is slowly heated to 33° C.-35° C. during one hour and continuously heated at 65° C.-70° C. for 2 hours. The hot suspension is filtered.

The sodium sulfate and charcoal are colleted and rinsed with hot ethanol (60 ml×2). The combined filtrates are concentrated to volume around 350 ml. The slurry is cooled around 10° C.-15° C. for 3 hours. The precipitated crystals are collected by filtration, rinsed with cooled ethanol (100 ml×2). The wet product is dried under vacuum around 70-80 mm/Hg and at 35° C.-40° C. under nitrogen flow to give product of 136.3 g (yield of 95.0%) with the purity of 99.5% (HPLC).

Melting point: 223° C.-225° C. (decomposed.)

Elemental analysis: Calculated: C, 58.37; H, 5.71; N, 11.35; Found: C, 58.30; H, 5.84; N, 11.41.

Water content (Karl-Fischer's Method): Calculated 2.43%, Found 2.48%.

IR: characteristic peak: 3440 cm-1

Powder X-Ray Diffraction Analysis: The pattern is the same with levofloxacin hemihydrate standard.

EXAMPLE 4

The Preparation of Levofloxacin Hemihydrate in Mixed Solvent System of Ethanol and Methyl Acetate Crude levofloxacin (60 g) is placed into a mixed system of ethanol (320 ml) and methyl acetate (320 ml) followed by the addition of sodium sulfate decahydrate (32 g) and activated carbon (2 g). The mixture is slowly heated to 33° C.-35° C. during one hour and continuously heated at 65° C.-70° C. for 1 hours. The hot suspension is filtered.

The sodium sulfate and charcoal are colleted and rinsed with mixed solvents of ethanol and methyl acetate (30 ml×2). The combined filtrates are re-heated to reflux for 30 minutes and cooled in air for 1 hour. After continuously cooling around 10° C.-15° C. for 6 hours the precipitated crystals are collected by filtration. The wet product is dried under vacuum around 80-90 mm/Hg and at 35° C.-40° C. under nitrogen flow to give 59.1 g (yield of 95.7%) of product with the purity of 99.5% (HPLC).

Melting point: 223° C.-225° C. (decomposed.)

Elemental analysis: Calculated: C, 58.37; H, 5.71; N, 11.35; Found: C, 58.33; H, 5.80; N, 11.29.

Water content (Karl-Fischer's Method): Calculated 2.43%, Found 2.48%.

IR: characteristic peak: 3440 cm-1

Powder X-Ray Diffraction Analysis: The pattern is the same with levofloxacin hemihydrate standard.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as preferably described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A process to selectively produce a pyridobenzoxazine carboxylic acid hemihydrate, comprising:
    mixing crude pyridobenzoxazine carboxylic acid and a calculated amount of sodium sulfate decahydrate in an anhydrous solvent system to form a mixture;
    heating the mixture to form pyridobenzoxazine carboxylic acid hemihydrate, wherein the pyridobenzoxazine carboxylic acid is of formula (I):

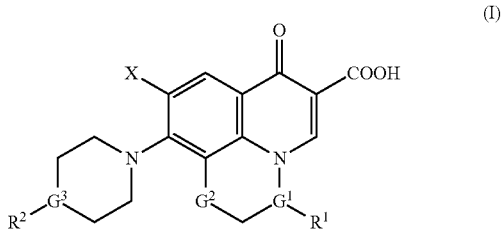

wherein X is halo; $G^1$ is carbon; $G^2$ is oxygen; $G^3$ is carbon or nitrogen; $R^1$ is $C_1$-$C_4$ alkyl; and $R^2$ is $C_1$-$C_4$ alkyl.

2. The process of claim 1, wherein X is fluoro; $G^1$ is carbon, optionally having an S stereochemical configuration; $G^2$ is oxygen; $G^3$ is nitrogen; $R^1$ is $C_1$-$C_4$ alkyl; and $R^2$ is $C_1$-$C_4$ alkyl.

3. The process of claim 1, wherein the pyridobenzoxazine carboxylic acid is (S)-9-fluoro-3-methyl-10-(4-methyl-1-piperazinyl)-7-oxo-2, 3-dihydro-7H-pyrido- [1, 2, 3-de] [1, 4] benzoxazine-6-carboxylic acid.

4. The process of claim 1, wherein the anhydrous solvent system comprises a $C_1$-$C_4$ alkyl alcohol, a $C_3$-$C_4$ alkyl ketone, a $C_3$-$C_4$ alkyl ester, or combination thereof.

5. The process of claim 4, wherein
    the anhydrous alcohol is ethanol, 1-propanol, 2-propanol, or a combination thereof;
    the anhydrous ketone is acetone, 2-butanone, or a combination thereof; and
    the anhydrous ester is methyl acetate, ethyl acetate, or a combination thereof.

6. The process of claim 1, wherein the anhydrous solvent system is ethanol, 1-propanol, 2-propanol, acetone, 2-butanone, methyl acetate, ethyl acetate, or a combination thereof.

7. The process of claim 1, wherein a weight ratio of crude pyridobenzoxazine carboxylic acid to volume of anhydrous solvent system is 1: about 5 to 1: about 16 (w/v).

8. The process of claim 1, wherein said the ratio of the weight of sodium sulfate decahydrate to crude pyridobenzoxazine carboxylic acid is about 0.2:1.0 to about 0.8:1.0 (w/w).

9. The process of claim 1, wherein the heating is at a temperature of about 25° C. to about 75° C.

10. The process of claim 1, wherein a total period of heating is about 1 to about 5 hours.

11. The process of claim 1, further comprising
    filtering the mixture containing the hemihydrate to remove sodium sulfate to form a filtrate containing the hemihydrate;
    optionally reducing the volume of the filtrate; and
    cooling the filtrate to form hemihydrate crystals.

12. The process of claim 11, further comprising
    collecting the hemihydrate crystals; and
    drying the hemihydrate crystals under vacuum and an inert atmosphere.

13. The process of claim 11, wherein the cooling is at a temperature of about 0° C. to about 20° C.

14. The process of claim 11, wherein the period of cooling is about 1 to about 24 hours.

15. The process of claim 12, further comprising drying the wet hemihydrate crystals under controlled conditions to prevent loss of crystal water and prevent conversion to anhydrous form.

16. The process of claim 15, wherein the temperature of the drying is about 20° C. to about 50° C. and optionally under an inert atmosphere.

17. The process of claim 15, wherein the drying is under a vacuum of about 20 to about 100 mm/Hg and optionally under an inert atmosphere.

18. The process of claim 1, wherein the mixture further comprises activated carbon, wherein the activated carbon is removed with the sodium sulfate after the hemihydrate is formed.

19. The process of claim 18, wherein a weight of activated carbon is about 1 to about 5% of the weight of crude pyridobenzoxazine carboxylic acid.

20. The process of claim 1, wherein the crude pyridobenzoxazine carboxylic acid is treated with activated carbon prior to the mixing with the calculated amount of sodium sulfate decahydrate.

21. The process of claim 1 in which $G^3$ is nitrogen.

* * * * *